(12) United States Patent
Green

(10) Patent No.: US 6,454,129 B1
(45) Date of Patent: Sep. 24, 2002

(54) COLLAPSIBLE DISPENSING SYSTEM

(76) Inventor: Ronald D. Green, 13595 Cable Rd., Pataskala, OH (US) 43062

(*) Notice: Subject to any disclaimer, the term of this patent is extended or adjusted under 35 U.S.C. 154(b) by 0 days.

(21) Appl. No.: 09/787,752

(22) PCT Filed: Dec. 14, 1999

(86) PCT No.: PCT/US99/29285
§ 371 (c)(1),
(2), (4) Date: Jun. 21, 2001

(87) PCT Pub. No.: WO01/44065
PCT Pub. Date: Jun. 2, 2001

(51) Int. Cl.⁷ .............................................. B65D 35/22
(52) U.S. Cl. ........................... 222/94; 222/95; 222/105; 222/136; 222/326
(58) Field of Search ............................. 222/94, 95, 96, 222/105, 136, 137, 145.6, 326

(56) References Cited

U.S. PATENT DOCUMENTS

| 4,340,154 A | * | 7/1982 | VanManen | 222/94 |
| 4,528,180 A | * | 7/1985 | Schaeffer | 222/94 |
| 4,801,046 A | * | 1/1989 | Miczka | 222/95 |
| 5,593,066 A | * | 1/1997 | Konuma et al. | 222/94 |

* cited by examiner

Primary Examiner—Joseph A. Kaufman
(74) Attorney, Agent, or Firm—Richard L. Huff

(57) ABSTRACT

A collapsible dispensing system for viscous fluids which should not be mixed until the time of application. The system comprises a cartridge and a container which fits into the cartridge. The cartridge is designed to fit into conventional caulking guns. The cartridge has a forward end cap having a central circular orifice and a rear thrust wall. The container fits into the cartridge and is made up of a plurality of collapsible chambers which hold the viscous fluids. The chambers may take the form of closed bags or accordion cylinders. At the front end of each chamber is a forward end piece. The forward end pieces fit snugly together and form a circular periphery. The forward end piece contains a neck which fits through the forward end cap and attaches to a mixing nozzle. Chambers having predetermined ratios of ingredients may be used in this system.

18 Claims, 4 Drawing Sheets

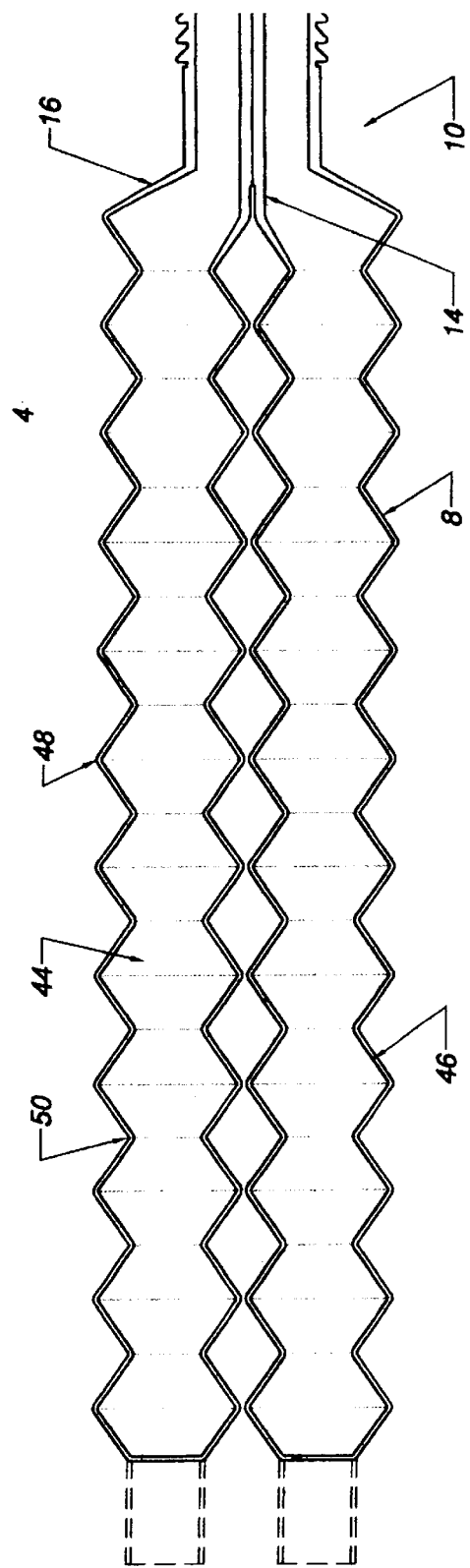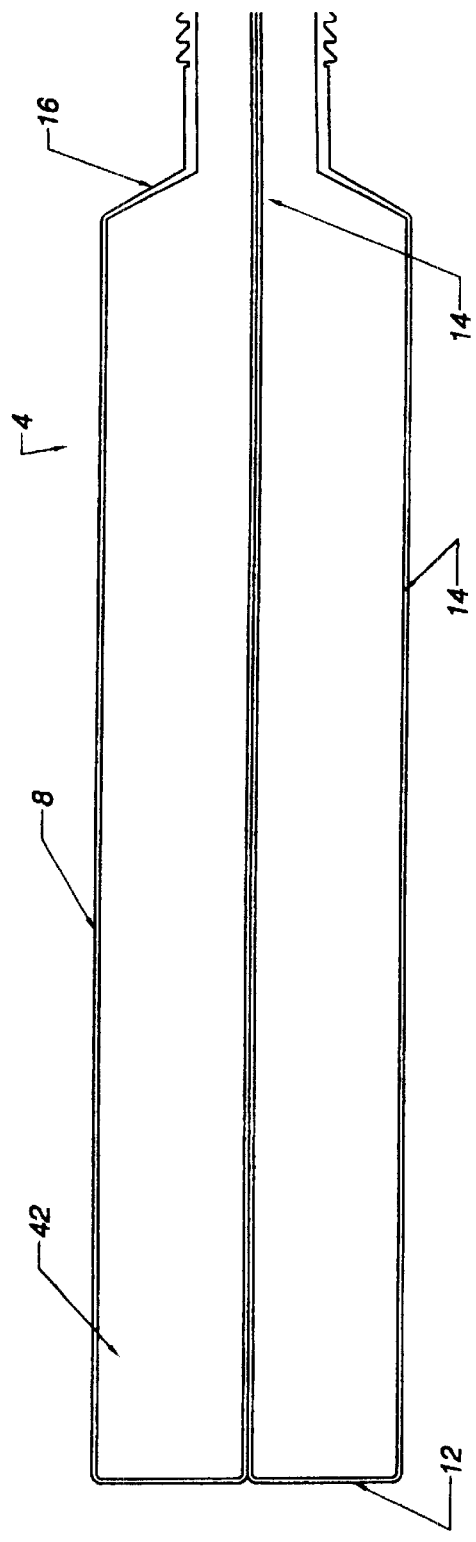

COLLAPSIBLE DISPENSING SYSTEM

TECHNICAL FIELD

The technical field of this invention relates to devices for the dispensing of non-solid, viscous materials.

BACKGROUND ART

Cartridges for storing and dispensing viscous materials such as resins, sealing compositions, dental compositions, or insulation compositions are known in the art. Such cartridges generally comprise an outer casing containing at one end, an end piece which attaches to an application nozzle and at the other end, a rear thrust wall designed to slide toward the end piece and force the viscous material out of the nozzle. This sliding of the rear thrust wall is brought about by a piston which is generally an integral part of a manual operating device, usually in the form of a gun equipped with a rack or friction advance mechanism.

Some viscous products consist of several viscous components which must be mixed, in given proportions, only at the time of application. It is known in the art to store the viscous components in multiple containers inside cartridges in such a way that the advancing rear Thrust wall will force the components through a single mixing nozzle whereby the components become mixed at the time of application.

U.S. Pat. No. 5,339,992 to Barthomeuf et al discloses a cartridge comprising an outer casing and an inner casing. Each casing holds a viscous component of a final product. The cartridge has a front end piece for receiving an application nozzle and a rear thrust wall which drives the components forward and through the nozzle when it is advanced.

The closest prior art known to the inventor are U.S. Pat Nos. 5,161,715, 5,184,757, and 5,242,082 to Giannuzzi. These patents disclose a double-barreled gun designed to inject a two-component epoxy composition. The gun contains two parallel barrels, each containing a foil pack containing viscous components of the final epoxy composition. The gun contains two front end pieces which are adapted to send the components into a mixing nozzle. The gun contains two pistons for urging the foil packs forward. As the foil packs are urged forward, cutting elements in the forward end of each barrel slit the foil packs and allow for the discharge of the stored components.

U.S. Pat. No. 3,767,085 to Cannon et al, U.S. Pat. No. 5,722,829 to Wilcox et al, and U. S. Pat. No. 5,875,928 to Muller et al are similar to each other in that each of these references discloses a double-barreled cartridge capable of receiving two parallel containers containing viscous materials which should be mixed only at the time of application. Each container empties into a front end piece which passes the viscous components to a mixing nozzle. Each container has a rear thrust wall which may be forced forward to expel the contents of the container into the front end piece.

Thus, cartridges and guns for these cartridges for use with viscous components which must be kept separate from each other are well known in the art. One problem which exists is the incompatibility of the cartridge of one manufacturer with the gun of another manufacturer or even the gun of the same manufacturer with a different size cartridge. Thus, a multiplicity of guns and cartridges are on the market, only a few of which are compatible.

DISCLOSURE OF INVENTION

The inventor recognized this problem and solved it by providing a cartridge which fits common caulking guns and which holds a container made up of a plurality of material chambers which hold viscous ingredients which should be kept separate until the time of application. The cartridge and containers are designed for a single use, and are constructed of recyclable materials. The chambers may have a variety of ratios of the several components.

The cartridge contains a tubular casing, a forward end cap having an orifice capable of snugly holding a piece capable of coupling with a conventional mixing nozzle, and a rear thrust wall capable of being urged forward by the piston of a conventional caulking gun.

The container is made up of multiple collapsible chambers containing closed rear ends, closed side edges, at least one edge being in common for at least a portion of the length of a side, and a forward end in which the forward edges of the chambers are sealed to a forward end piece. The collapsible chambers may be sealed bags made of sturdy plastic or expandable and compressible chambers having accordion configurations. Each forward end piece has a body portion, a shoulder portion, and a neck portion. When in position in the cartridge, the multiple body portions of the end piece will form a circle which will abut with the cartridge, the shoulder portions will abut with the end cap, and the neck portion will snugly fit through an orifice in the end cap to engage a mixing nozzle.

BRIEF DESCRIPTION OF DRAWINGS

FIG. 3 is a cross-sectional view of an expanded accordion container.

FIG. 4 is a cross-sectional view of an expanded bag container.

BEST MODE FOR CARRYING OUT THE INVENTION

Figure 1:
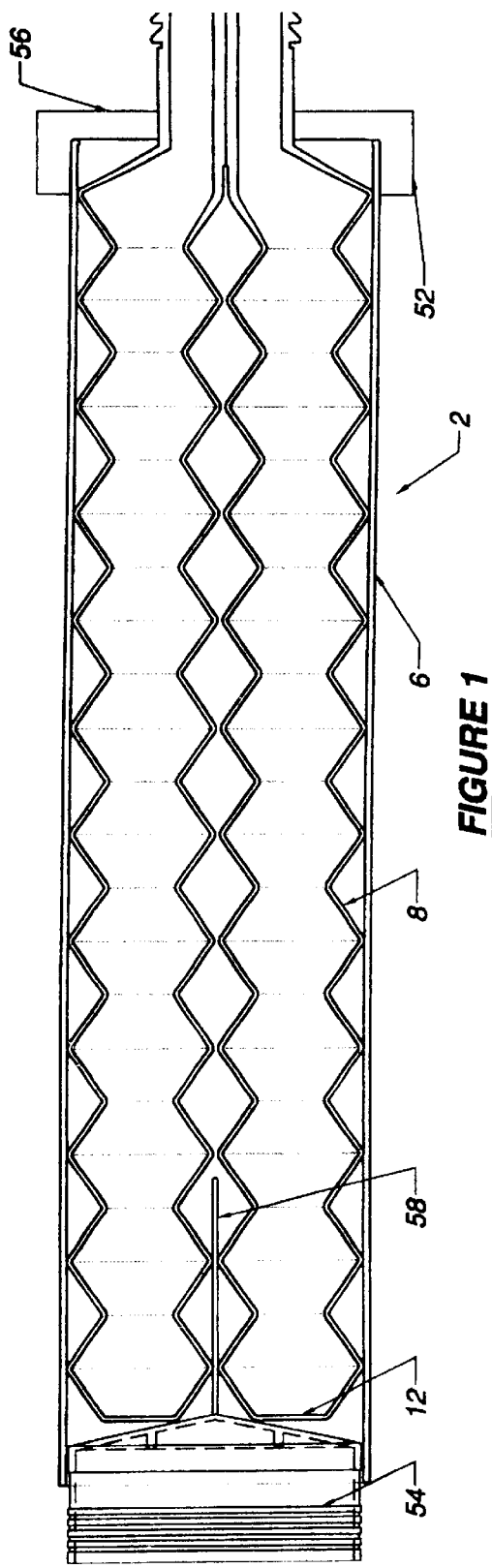
FIG. 1 is a cross-sectional view of a system having a cartridge containing an expanded accordion container.
Figure 2:
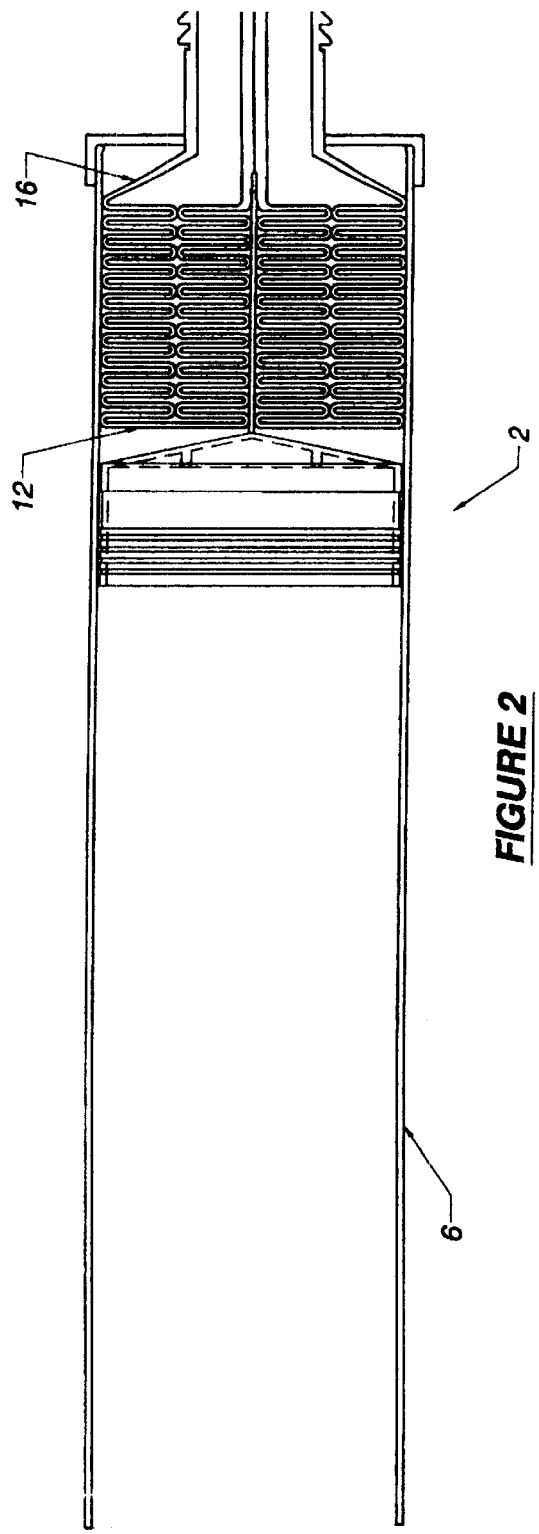
FIG. 2 is a cross-sectional view of a system having a cartridge containing a collapsed accordion container.
Figure 6:
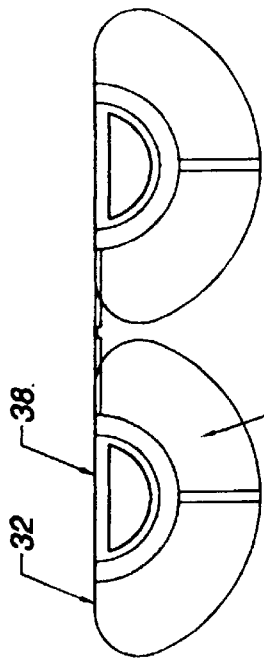
FIG. 6 is an end view of a two-part forward end piece in the open position.
Figure 8:
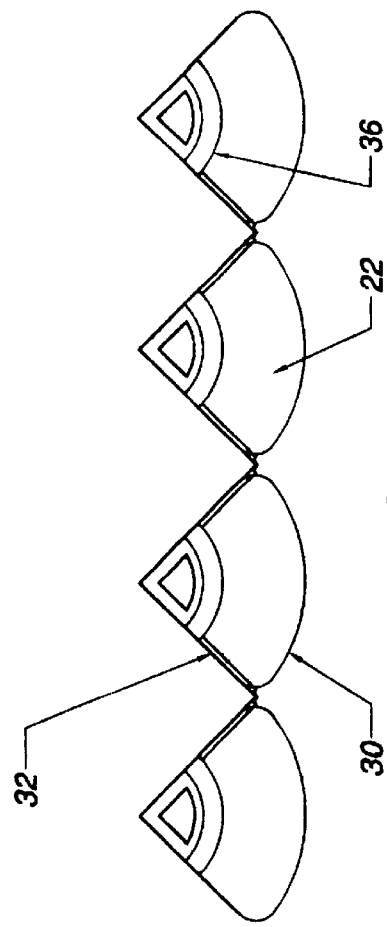
FIG. 8 is an end view of a four-part forward end piece in the open position.
Figure 5:
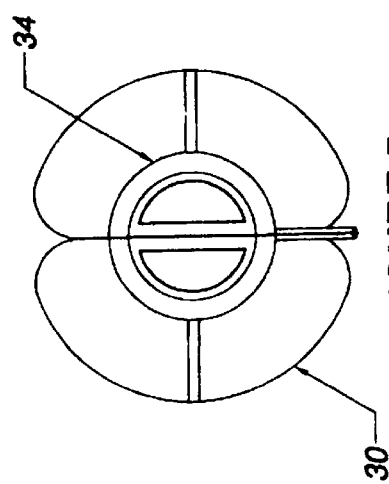
FIG. 5 is an end view of a two-part forward end piece in the closed position.
Figure 7:
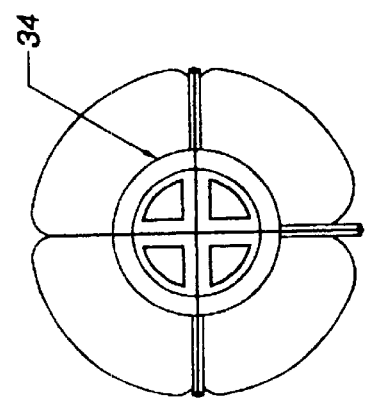
FIG. 7 is an end view of a four-part forward end piece in the closed position.
Figure 10:
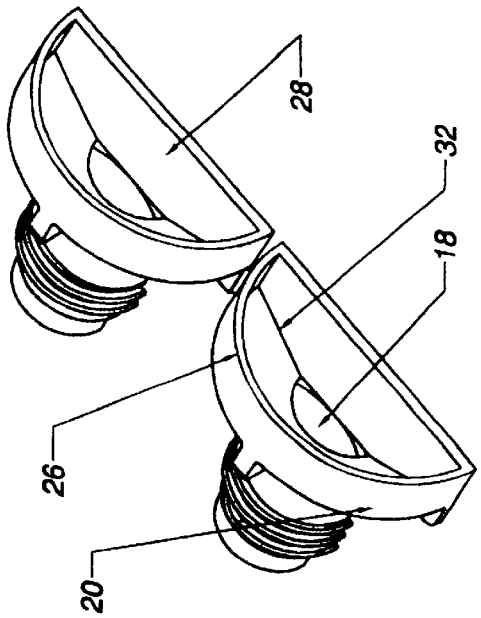
FIG. 10 is another elevational perspective view of a two-part forward end piece in the open position.
Figure 9:
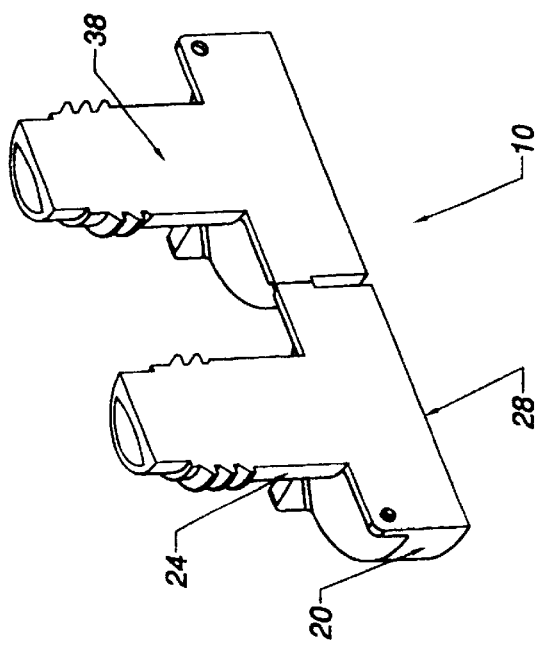
FIG. 9 is an elevational perspective view of a two-part forward end piece in the open position.
Figure 11:
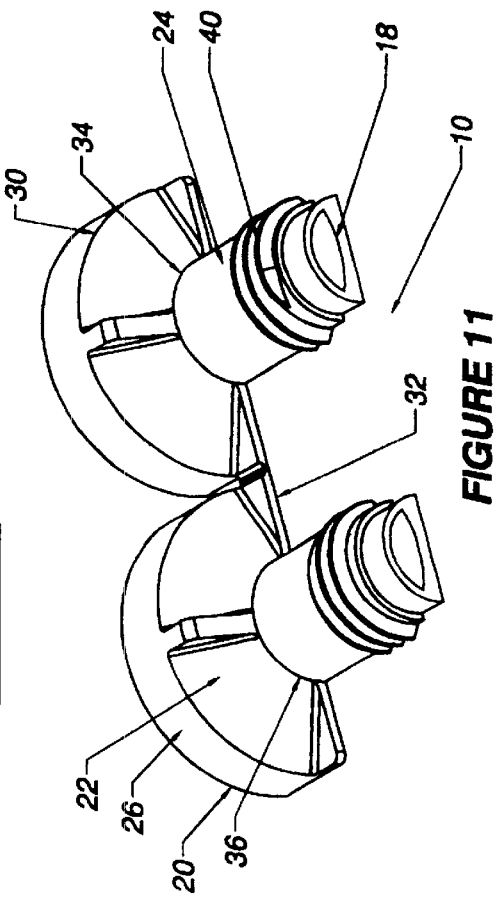
FIG. 11 is still another elevational perspective view of a two-part forward end piece in the open position.

The invention will now be described in detail with reference to the above drawings. Like numbers refer to like parts throughout the description.

The collapsible dispensing system 2 of this invention is useful for the dispensing of viscous materials which should be kept separate until the time of application. Examples of such materials are epoxy resins which contain a resin and a catalyst, sealing compositions, and insulation compositions.

The system 2 is made up of a container 4 for the viscous materials and a cartridge 6 for the container 4.

The container 4 comprises at least two chambers 8 and a forward end piece 10. Each chamber 8 will be filled with a viscous material which should be kept separate from the other material during storage. Each chamber 8 contains a closed rear end 12; closed side edges 14, at least one of the closed side edge 14 being common with at least one other chamber 8 for at least a portion of its length; and a forward edge 16. The forward edge 16 of each chamber 8 is attached to a separate or unified forward end piece 10.

The forward end piece 10 of the container 4 is a hollow body which forms a passageway 18 between the inside of the chamber 8 and a mixing nozzle (not shown). Mixing nozzles are well known in the art, and do not constitute a part of the present invention. The forward end piece 10 comprises a body portion 20, a shoulder portion 22, and a neck portion 24. The body portion 20 has an arcuate peripheral edge 26 and a straight central edge 28. The shoulder portion 22 connects the body portion 20 and the neck portion 24 and forms the front end of the chamber 8. The shoulder portion 22 is bounded by an arcuate peripheral edge 30 which abuts with the arcuate peripheral edge 26 of the body portion 20, a straight central edge 32, and an arcuate central edge 34. The neck portion 24 is an elongated piece having an arcuate peripheral edge 36 which abuts with the arcuate central edge 34 of the shoulder portion 22 and a straight central edge 38. While in storage, the neck portion 24 is closed by a friction-fit or threaded closure (not shown). The neck portion 24 will attach to a conventional mixing nozzle by a friction fit or by threads 40. While the several portions have been described separately, it is preferable that the forward end piece 10 be manufactured as a single unit.

The body portion 20, shoulder portion 22, and neck portion 24 are shaped such that when a plurality of forward end pieces 10 are fitted together, the arcuate peripheral edges 26, 30,36 form circles and the straight central edges 28,32, 38 fit snugly together. Thus, if the container 4 is made up of two chambers 8, and therefore has two forward end pieces 10, each body portion 20 will take the form of a semi-circle when viewed endwise. When placed into the cartridge 6, each straight central edge 28,32,38 fits flat against the straight central edge 28, 32,38 of the other and the outer configuration forms a circle. If the container 4 is made up of three chambers 8, and therefore has three forward end pieces 10, each body portion 20 will take the form of a third of a circle (120°) when viewed endwise. When placed into the cartridge 6, each straight edge 28,32,38 will fit snugly with the others.

The containers 4 must be air-tight, collapsible, and made of material which economically justifies disposal and recycling of the system 2 following use.

One form of chamber 8 is made of sturdy flexible material, such as plastic or rubber, and is in the form of a closed bag 42. The chamber 8 has a closed rearward end 12; at least one closed side edge 14, at least one closed side edge 14 being in common with at least one other chamber 8 for at least a portion of its length, and the forward edge 16 of the chamber 8 is connected to the forward end piece 10. The chambers 8 may be manufactured using conventional means for making plastic bags, but including the additional step of joining at least two such chambers 8 together with a heat seal or chemical bonding agents. The chambers 8 may be joined throughout their entire length or for some other desired shorter distance. Heat seals are preferred, but conventional chemical bonding agents are acceptable for the purpose of creating closures between the chambers 8. The end pieces 10 are preferably made of one-piece molded plastic.

Another form of chamber 8 according to this invention is made up of sturdy, shape-retaining, but flexible material, such as plastic or rubber and has an accordion configuration 44. The chamber 8 has a closed rearward end 12, a body 46 having circumferential peaks 48 and valleys 50, at least one side edge 14 in common with, or slightly separated from, at least one other chamber 8, and the forward edge 16 of the chamber 8 is connected to the forward end piece 10. The chambers 8 may be manufactured using conventional means for making collapsible plastic or rubber bottles, but including the additional step of joining at least two such chambers 8 together with a heat seal or chemical bonding agents. The chambers 8 may be joined throughout their entire length or for some other desired shorter distance. As the end piece 10 is required to be firm and unyielding and the body of the chamber must be flexible, it is not recommended that the body of the chamber 8 and the end piece 10 be manufactured of the same material. As above, the end piece 10 is preferably manufactured of one piece molded plastic.

Chambers 8 having the same or different volumes may be supplied in a single container 4. Thus, when 1:1 ratios of materials are desired for a two-chamber container 4, each chamber 8 is of the same length and has the same cross-sectional area. Where ratios other than 1:1 are desired, such as 2:1, 5:1, or 10:1 for two-chambered containers, the length of the chambers 8 remains the same, and the cross-sectional areas are adjusted to provide the desired volumes. The same principle applies for three or more chambers 8. This enables the user to select a single container 4 for procedures requiring one ratio of materials and another single container 4 for another procedure requiring a different ratio of materials. Thus, unlike the prior art containers, a single cartridge 6 and a single gun (not shown) will be suitable for all containers 4 regardless of the ratio of materials required by the procedure. If only a portion of the material is used, the neck portion 24 of the forward end piece 10 may be closed with a threaded or friction-fit closure (not shown), thus preventing the materials from being exposed to air.

The system 2 is designed for one-time use. Therefore the cartridge 6, forward end cap 52 and rear thrust wall 54 are made of recyclable materials. The tubular cartridge 6 may be made of metal, cardboard, or sturdy shape-holding plastic. The forward end cap 52 is preferably made of flexible rubber or plastic so as to achieve easy application to, and removal from the cartridge 6. The forward end cap 52 contains a centrally located circular orifice 56 which provides for a snug fit with the neck 24 of the forward end pieces 10 of the container 4. The rear thrust wall 54, which preferably contains a forward extension 58, is preferably made of metal or plastic. The size of the rear thrust wall 54 allows easy sliding within the tubular cartridge 6.

The chambers 8 may be filled with the viscous materials by forcing the viscous material under pressure into the proper chambers through the forward end pieces 10.

In use, the container 4 comprising a plurality of filled chambers 8 is placed into the cartridge 6 and the assembled system 2 is placed into a conventional caulking gun. The rear thrust wall 54 is impelled forwardly, causing the viscous materials in each of the chambers 8 to be expelled through the necks 24 of the front end pieces 10 to be mixed in the mixing nozzles.

The materials will be expelled in direct ratio to the volumes of the chambers 8. Thus, the required, pre-selected ratios are available to the user.

INDUSTRIAL APPLICABILITY

A system for dispensing viscous materials which should not be mixed until the time of application is made up of a cartridge and a container which fits into the cartridge. The cartridge fits into conventional caulking guns, thus eliminating the need for multiple, unique guns. The cartridge is simple in nature, containing a rear thrust wall which slides forward when impelled by the piston of a gun, and a forward end wall containing a central orifice. The container is made up of a plurality of collapsible chambers for holding the viscous materials.

The chambers may be in the form of sealed collapsible bags or may have an accordion configuration. The chambers may be of any predetermined volume ratio. As the rear thrust wall is impelled forwardly, the chambers holding the separate viscous materials collapse and the viscous materials are forced through forward end pieces. The forward end pieces are formed such that when fitted together, they fit together snugly and form a circle as their outer configuration. The forward end pieces contain necks which carry the still-separated viscous materials to a mixing nozzle for mixing and application to the desired site.

What is claimed is:

1. In a container for a collapsible dispensing system for viscous materials which should be kept separate until the time of application, the improvement wherein the container comprises at least two chambers containing closed rear ends, closed side edges, a forward edge, and at least one side which is common between two chambers for at least a portion of their lengths, and wherein the forward edge of each chamber is connected to a forward end piece, the forward end piece comprises a body portion, a shoulder portion, and a neck portion adapted to attach to a mixing nozzle; the body portion has an arcuate peripheral edge and a central edge; the shoulder portion connects the body portion and the neck portion and forms a front end of the chamber, the shoulder portion has an arcuate peripheral edge which abuts with the arcuate peripheral edge of the body portion, a straight central edge, and an arcuate central edge; the neck portion is an elongated piece having a rearward end and a forward end, an arcuate peripheral edge which, at its rearward end, abuts with the arcuate central edge of the shoulder portion, and a straight central edge; the body portion, shoulder portion, and neck portion being shaped such that when the forward end pieces are fitted together, the arcuate peripheral edges form a circle and the straight central edges fit snugly together.

2. The container of claim 1 wherein, the chambers are in the form of collapsible bags.

3. The container of claim 2 wherein, the chambers are made of sturdy plastic or rubber.

4. The container of claim 3 wherein, there are two chambers of equal volume.

5. The container of claim 3 wherein, there are a plurality of chambers having volumes having predetermined ratios.

6. The container of claim 1 wherein, the chambers have an accordion configuration.

7. The container of claim 6 wherein, the chambers are made of sturdy plastic or rubber.

8. The container of claim 7 wherein, there are two chambers of equal volume.

9. The container of claim 7 wherein, there are a plurality of chambers having volumes having predetermined ratios.

10. In a collapsible dispensing system for viscous materials which should be kept separate until the time of application, the improvement wherein the collapsible dispensing system comprises:
a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and
b) the container of claim 1 wherein the neck portion of the forward end piece of the container fits snugly in the circular orifice of the forward end wall.

11. In a collapsible dispensing system for viscous materials which should be kept separate until the time of application, the improvement wherein the collapsible dispensing system comprises:
a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and
b) the container of claim 2 wherein the neck portion of the forward end piece of the container fits snugly in the circular orifice of the forward end wall.

12. In a collapsible dispensing system for viscous materials which should be kept separate until the time of application, the improvement wherein the collapsible dispensing system comprises:
a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and
b) the container of claim 3 wherein the neck portion of the forward end piece of the container fits snugly in the circular orifice of the forward end wall.

13. In a collapsible dispensing system for viscous materials which should be kept separate until the time of application, the improvement wherein the collapsible dispensing system comprises:
a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and
b) the container of claim 4 wherein the neck portion of the forward end piece of the container fits snugly in the circular orifice of the forward end wall.

14. In a collapsible dispensing system for viscous materials which should be kept separate until the time of application, the improvement wherein the collapsible dispensing system comprises:
a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and
b) the container of claim 5 wherein the neck portion of the forward end piece of the container fits snugly in the circular orifice of the forward end wall.

15. In a collapsible dispensing system for viscous materials which should be kept separate until the time of application, the improvement wherein the collapsible dispensing system comprises:

a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and b) the container of claim 6 wherein the neck portion of the forward end piece of the container fits snugly in the circular orifice of the forward end wall.

16. In a collapsible dispensing system for viscous materials which should be kept separate until the time of application, the improvement wherein the collapsible dispensing system comprises:

a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and b) the container of claim 7 wherein the neck portion of the forward end piece of the container fits snugly in the circular orifice of the forward end wall.

17. In a collapsible dispensing system for viscous materials which should be kept separate until the time of application, the improvement wherein the collapsible dispensing system comprises:

a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and b) the container of claim 8 wherein the neck portion of the forward end piece of the container fits snugly in the circular orifice of the forward end.

18. In a collapsible dispensing system for viscous materials which should be kept separate until the time of application, the improvement wherein the collapsible dispensing system comprises:

a) a cartridge having a rearward end and a forward end, a rear thrust wall which is slidably mounted at the rearward end, and a forward end wall having a side and a forward cover, which forward end wall frictionally fits onto the forward end of the cartridge, the forward cover of the forward end wall contains a circular orifice, and b) the container of claim 9 wherein the neck portion of the forward end piece of the container fits snugly in the circular orifice of the forward end wall.

* * * * *